US00PP16824P2

(12) United States Plant Patent
Verthoef

(10) Patent No.: US PP16,824 P2
(45) Date of Patent: Jul. 18, 2006

(54) ***WEIGELA* PLANT NAMED 'VERWEIG'**

(50) Latin Name: *Weigela florida*
Varietal Denomination: Verweig

(75) Inventor: Bert Verthoef, Hazerswoude Dorp (NL)

(73) Assignee: Spring Meadow Nursery, Inc., Grand Haven, MI (US)

( * ) Notice: Subject to any disclaimer, the term of this patent is extended or adjusted under 35 U.S.C. 154(b) by 27 days.

(21) Appl. No.: 11/108,574

(22) Filed: Apr. 15, 2005

(51) Int. Cl.
*A01H 5/00* (2006.01)

(52) U.S. Cl. ..... Plt./226

(58) Field of Classification Search ..... Plt./226
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Weigela* plant named 'Verweig', characterized by its compact, upright and outwardly spreading plant habit; freely branching habit; green, white and red purple variegated leaves; and tolerance to high and low temperatures.

2 Drawing Sheets

Botanical designation: *Weigela florida.*
Cultivar denomination: 'Verweig'.

BACKGROUND OF THE INVENTION

The present Invention relates to a new and distinct cultivar of *Weigela* plant, botanically known as *Weigela florida*, and hereinafter referred to by the name 'Verweig'.

The new cultivar is a naturally-occurring branch mutation of the *Weigela florida* Tango, not patented. The cultivar Verweig was discovered and selected by the Inventor within a population of plants of the parent cultivar in a controlled environment in Hazerwoude Dorp, The Netherlands in 2001.

Asexual reproduction of the new *Weigela* by softwood cuttings at Hazerwoude Dorp, The Netherlands since 2001, has shown that the unique features of this new *Weigela* are stable and reproduced true to type in successive generations of asexual reproduction.

SUMMARY OF THE INVENTION

The following traits have been repeatedly observed and are determined to be the unique characteristics of 'Verweig'. These characteristics in combination distinguish 'Verweig'as a new and distinct cultivar:

1. Compact, upright and outwardly spreading plant habit.
2. Freely branching habit.
3. Green, white and red purple variegated leaves.
4. Tolerance to high and low temperatures.

Plants of the new *Weigela* differ primarily from plants of the parent, the cultivar Tango, in the following characteristics:

1. Plants of the new *Weigela* are more compact with shorter internodes than plant of the cultivar Tango.
2. Plants of the new *Weigela* have smaller leaves with shorter petioles than plants of the cultivar Tango.
3. Plants of the new *Weigela* and the cultivar differ in leaf coloration as plants of the cultivar Tango do not have variegated foliage.

Plants of the new *Weigela* can be compared to plants of the Weigela cultivar Nana Variegata, not patented. However, plants of the new *Weigela* differ from plants of 'Variegata' in leaf coloration as leaves of plants of 'Nana Variegata' are green and white in color.

BRIEF DESCRIPTION OF THE PHOTOGRAPHS

The accompanying colored photographs illustrate the overall appearance of the new *Weigela,* showing the colors as true as it is reasonably possible to obtain in colored reproductions of this type. Colors in the photographs may differ slightly from the color values cited in the detailed botanical description which accurately describe the colors of the new *Weigela.*

The photograph at the top of the first sheet is a close-up view of typical leaves of 'Verweig'.

The photograph at the bottom of the first sheet comprises a side perspective view of a typical plant of 'Verweig'.

The photograph on the second sheet is a close-up view of typical flowers of 'Verwig'.

DETAILED BOTANICAL DESCRIPTION

The new *Weigela* has not been observed under all possible environmental conditions. The phenotype may vary somewhat with variations in environment such as temperature and light intensity, without, however, any variance in genotype.

The aforementioned photographs, following observations and measurements describe plants grown in Grand Haven, Mich. during the spring and summer in an outdoor nursery and under commercial production practices. Plants were about 2.5 years old when the photographs and the description were taken.

In the following description, color references are made to The Royal Horticultural Society Colour Chart, 2001 Edition, except where general terms of ordinary dictionary significance are used.

Botanical classification: *Weigela florida* cultivar Verweig.

Parentage: Naturally-occurring branch mutation of *Weigela florida* cultivar Tango, not patented.

Propagation:

*Type*.—Softwood cuttings.

*Time to initiate roots*.—About 15 days at 25° C.

*Time to produce a rooted young plant*.—About two months at 25 ° C.

*Root description*.—Fine; soft brown in color.

*Rooting habit*.—Freely branching; dense.

Plant description:

*Plant form*.—Compact, upright and outwardly spreading perennial shrub; mounded plant habit.

*Growth habit*.—Vigourous; dense and bushy growth habit.

*Plant height*.—About 24 cm.

*Plant width* (*spread*).—About 40 cm.

*Lateral branches*.—Quantity per plant: Freely branching habit, about 74. Length: About 8 cm. Diameter: About 2 mm. Internode length: About 1 cm. Strength: Strong. Texture: Young stems, pubescent; older stems, smooth, glabrous. Color: 177C.

*Foliage description*.—Arrangement: Opposite, simple. Length: About 7.3 cm. Width: About 3 cm. Shape: Elliptic to ovate. Apex: Acute. Base: Attenuate. Margin: Serrulate. Texture, upper surface: Rugose; glabrous. Texture, lower surface: Ruguse; pubescent. Venation pattern: Pinnate. Color: Developing leaves, upper and lower surfaces: Center, 141A; towards the margins 158A and 183A. Fully expanded leaves, upper and lower surfaces: Center, 141A; towards the margins 158A and occasionally, 183A. Venation, upper surface: 145A. Venation, lower surface: 145B. Petiole: Length: About 2 mm. Diameter: About 3 mm. Color, upper and lower surfaces: 145B.

Flower description:

*Flower type and habit*.—Single dark pink-colored campanulate flowers; mostly axillary; about three to seven flowers per lateral branch. Flowers not persistent. Flowers face outward or are drooping.

*Natural flowering season*.—Plants flower during May and June in Grand Haven, Mich.

*Postproduction longevity*.—Flowers typically last about two to four weeks on the plant.

*Fragrance*.—None detected.

*Flower buds*.—Height: About 3 mm. Diameter: About 2.5 mm. Shape: Ovoid. Color: 198D.

*Flowers*.—Diameter: About 2 cm. Depth: About 3.5 cm.

*Petals*.—Quantity per flower: Five, fused at base. Length: About 6 mm. Width: About 1 cm. Shape: Rounded lobes. Apex: Obtuse. Margin: Entire. Texture, upper and lower surfaces: Smooth, glabrous. Color: When opening, upper surface: 71D. When opening, lower surface: 71A. Fully opened, upper surface: 71C; longitudinal stripe, 15B. Fully opened, lower surface: 71D.

*Sepals*.—Quantity per flower: Five, fused at base. Length: About 5 mm. Width: About 1 mm. Shape: Linear. Apex: Acute. Margin: Entire. Texture, upper and lower surfaces: Smooth; glabrous. Color, upper and lower surfaces: 198D.

*Peduncles*.—Length: About 1 cm. Diameter: About 2 mm. Orientation: About 20° from vertical. Strength: Moderately strong. Color: Close to 144A.

*Reproductive organs*.—Stamens: Quantity per flower: About five. Anther shape: Narrowly oblong. Anther length: About 3 mm. Anther diameter: About 1 mm. Anther color: 198D. Pollen amount: Scarce. Pollen color: 198C. Pistils: Quantity per flower: One. Pistil length: About 3.5 cm. Stigma shape: Globular, flattened. Stigma color: 158C. Style length: About 3.4 cm. Style color: 158C. Ovary color: Close to 143C.

*Seed/fruits*.—Seed and fruit development have not been observed.

Disease/pest resistance: Plants of the new *Weigela* have not been observed to be resistant to pathogens and pests common to *Weigela*.

Temperature tolerance: Plants of the new *Weigela* have been observed to tolerate temperatures ranging from −30 to 38° C.

It is claimed:

1. A new and distinct cultivar of *Weigela* plant named 'Verweig', as illustrated and described.

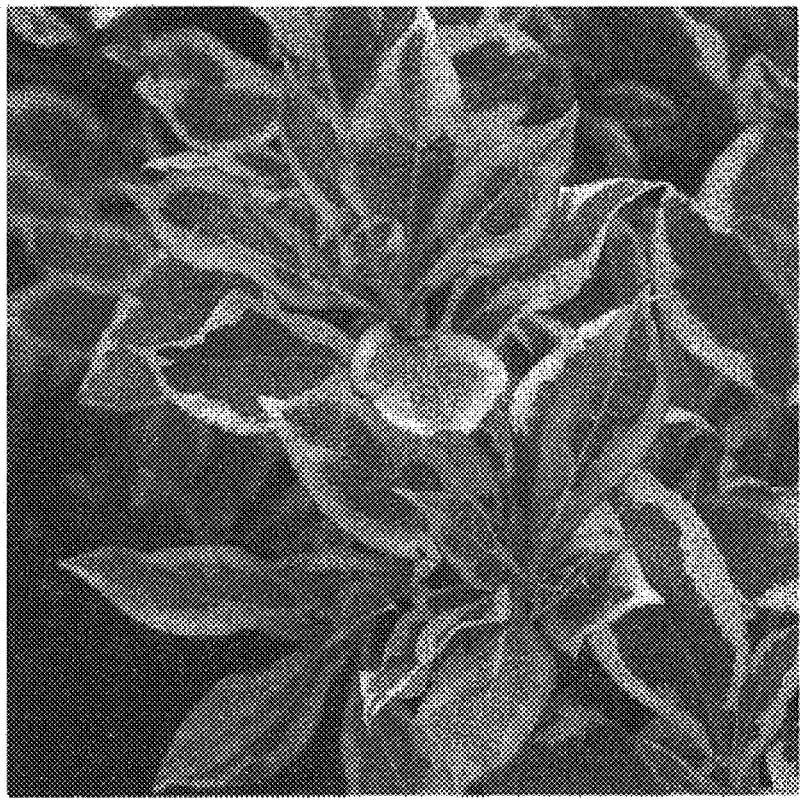
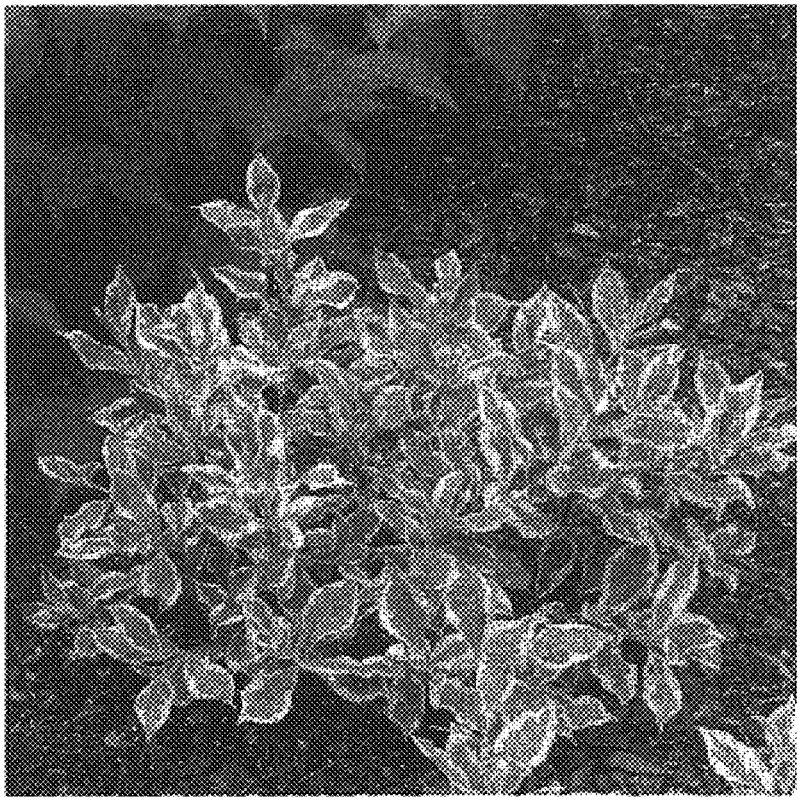

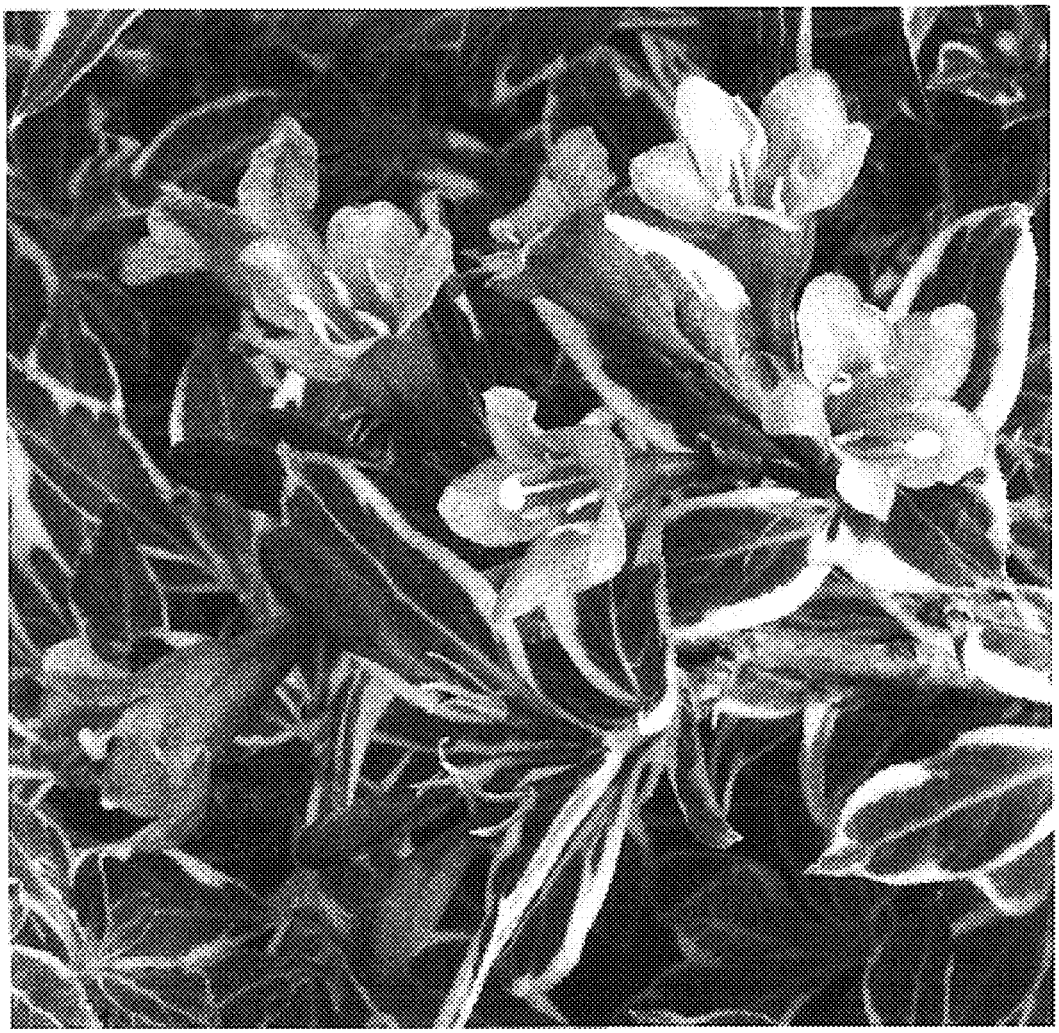

* * * * *